(12) United States Patent
Lussey (10) Patent No.: US 12,055,508 B2
(45) Date of Patent: Aug. 6, 2024

(54) ELECTRICAL CHARGE STORAGE MEDIUM

(71) Applicant: David Lussey, Richmond (GB)

(72) Inventor: David Lussey, Richmond (GB)

(*) Notice: Subject to any disclaimer, the term of this patent is extended or adjusted under 35 U.S.C. 154(b) by 308 days.

(21) Appl. No.: 16/474,454

(22) PCT Filed: Dec. 27, 2017

(86) PCT No.: PCT/GB2017/053893
§ 371 (c)(1),
(2) Date: Jun. 27, 2019

(87) PCT Pub. No.: WO2018/122556
PCT Pub. Date: Jul. 5, 2018

(65) Prior Publication Data
US 2020/0217810 A1    Jul. 9, 2020

(30) Foreign Application Priority Data
Dec. 27, 2016  (GB) .................................. 1622299
Jun. 13, 2017  (GB) .................................. 1709372

(51) Int. Cl.
*G01N 27/12*   (2006.01)
*G01N 33/00*   (2006.01)
*H01M 10/02*   (2006.01)

(52) U.S. Cl.
CPC ....... *G01N 27/126* (2013.01); *G01N 33/0047* (2013.01); *H01M 10/02* (2013.01)

(58) Field of Classification Search
CPC .......................... G01N 27/126; G01N 33/0047
See application file for complete search history.

(56) References Cited

U.S. PATENT DOCUMENTS 5,541,570 A * 7/1996 McDowell ........... H01C 10/106
338/47
6,387,485 B1 * 5/2002 Bielek ....................... C09J 7/38
428/209

FOREIGN PATENT DOCUMENTS

EP    0699964    *   8/1994

OTHER PUBLICATIONS

Thermal and electrical properties of magnetite filled polymers Bernd Weidenfeller, Michael Hofer, Frank Schilling Composites: Part A 33 (2002) 1041-1053 (Year: 2002).*

(Continued)

*Primary Examiner* — Brian R Gordon
*Assistant Examiner* — Dwan A Gerido
(74) *Attorney, Agent, or Firm* — Jackson Walker LLP (57) ABSTRACT

An electrical charge storage medium comprises a quantity of first electrically conductive particles contained in a non conductive binder (for example polyurethane). The first electrically conductive particles are magnetite particles. The quantity of magnetite particles includes a distribution of particle sizes between sub-micron and tens of microns, and the magnetite particles have a plurality of planar faces, adjacent planar faces connected at a vertex. The particles each have a plurality of vertices. The magnetite particles are irregular in shape and have a low aspect ratio. Electrical charge storage medium is applied to a non-conductive substrate and contacted by two spaced apart electrodes to sense the change in resistance upon intercation with a volatile organic compound.

13 Claims, 5 Drawing Sheets

Mag 10 before milling (56) References Cited

OTHER PUBLICATIONS

Thermal, electrical, and magnetic studies of magnetite filled polyurethane shape memory polymers Muhammad Yasar Razzaq, Mathias Anhalt, Lars Frormann, Bernd Weidenfeller Materials Science and Engineering A 444 (2007) 227-235 (Year: 2007).*

* cited by examiner

Mag 10 before milling

FIGURE 1a

Mag 10 after milling

FIGURE 1b

Mag 25 before milling

FIGURE 2a

Mag 25 after milling

FIGURE 2b

SEM @ x1.00k

Mag 50 before milling

FIGURE 3a

Mag 50 after milling

ELECTRICAL CHARGE STORAGE MEDIUM

FIELD OF THE INVENTION

This invention relates to an electric charge storage medium containing shaped particles of conductive metals and/or metal oxides. Such particles can be made in a composite form using a binder and the mechanical and electrical qualities of the binder can be used synergistically with selected particulate filler morphology and amounts to produce a super-sensitive control charge composite storage medium which, when charged can be made to respond selectively to sense various stimuli and also provides an indication of the onset and amount of the stimulus by rate of change of the charge stored within the composite.

BACKGROUND OF THE INVENTION

Electrically conductive polymer composites which exhibit changing electrical resistance when subject to compressive or tensile forces are known. Also known are sensing composites which can be charged to respond to volatile organic compounds (VOCs) but these composites are erratic in operation having charge characteristics which cannot be controlled to provide real time repeatable resolution of the stimulus data.

SUMMARY OF THE INVENTION

According to the invention there is provided an electrical charge storage medium, wherein the medium is comprised of an electrically conductive filler within a non-conductive binder composition and wherein the amount of charge stored by the medium may be controlled by changing the relative amounts of electrically conductive filler to non-conductive binder and/or by adjusting the relative proportions, shape and size of the electrically conductive fillers.

According to a first aspect of the invention there is provided an electrical charge storage medium comprising a quantity of first electrically conductive particles contained in a non conductive binder, which first electrically conductive particles are magnetite particles, wherein the quantity of magnetite particles includes a distribution of particle sizes between sub-micron and tens of microns, and wherein the magnetite particles have a plurality of planar faces, adjacent planar faces connected at a vertex, the particles each having a plurality of vertices wherein the magnetite particles are irregular in shape and have a low aspect ratio.

Preferably, the shape of the first electrically conductive particles in the distribution fall under the particle shape definitions of, "oblate", that is tabular, and/or "bladed", that is a flat or elongated shape form.

Preferably, the distribution of particles the particle size of the first electrically conductive particles at $d_{50}$ is between 50 and 75 micron Preferably, the distribution of particles the particle size of the first electrically conductive particles at $d_{50}$ is between 60 and 65 micron.

Preferably, in the distribution of particles the particle size of the first electrically conductive particles at $d_{50}$ is be between 20 and 25 micron.

Preferably, in the distribution of particles the particle size of the first electrically conductive particles size at $d_{50}$ is be between 5 and 15 micron.

Preferably, particle size of the first electrically conductive particles at $d_{50}$ is around 10 micron.

Preferably, the distribution of particle sizes between sub-micron and tens of microns in the quantity of magnetite particles includes sub-micron sized particles and particles that are tens of microns 111 size.

The electrical charge storage medium may further comprise a second type of electrically conductive particle of a different shape to the first electrically conductive particle.

Advantageously, the second type of electrically conductive particle has one of the following shapes: void bearing, plate like, needle like and spherical.

The second type of electrically conductive particle may be selected from the group comprising: silver, nickel, copper, iron, oxides of silver, nickel copper and iron including but not limited to magnetite and synthetic magnetite.

The particle size of the second type of electrically conductive particles may be between 10 and 15 micron.

The binder may be a polymer binder.

Preferably, the polymer is one of: a silicone polymer, a polyurethane polymer; polyethylene and an acrylic polymer.

Advantageously, the binder forms a thin layer around each particle or agglomerations of particles in the particle distribution.

Preferably, the thickness of the thin layer is in the order of 10 nano-metres.

It is preferred that the particles and/or agglomerations of particles are coated with the thin layer of binder and wherein adjacent separate coated particles and/or agglomerations of particles are in contact with each other and wherein the charge storage medium is formed by a matrix of so coated particles and/or agglomerations of particles.

Advantageously, the proportion of magnetite particles to binder is greater than or equal to 33% by weight.

The proportion of magnetite particles to binder may be greater than or equal to 50% by weight.

The proportion of magnetite particles to binder may be greater than or equal to 66% by weight.

The proportion of magnetite particles to binder may be greater than or equal to 75% by weight.

The proportion of magnetite particles to binder may be greater than or equal to 83% by weight.

The proportion of magnetite particles to binder may be greater than or equal to 90%.

According to a second aspect of the invention there is provided a method of manufacturing an electrical charge storage medium according to the first aspect of the invention, the method comprising the step of:

mixing the electrically conductive particles with the binder until the mixture thereof is homogeneous.

The method of manufacturing an electrical charge storage medium may further comprise mixing of the electrically conductive particles with the binder is low shear mixing, the mixture being mixed by a low shear paddle or by folding.

The method of manufacturing an electrical charge storage medium may include the additional step of heating the binder to reduce the viscosity thereof, prior to and/or during the step of mixing the electrically conductive particles with the binder.

The method of manufacturing an electrical charge storage medium may include the additional step of drying the resulting mixture.

The method of manufacturing an electrical charge storage medium may include the additional steps of: specifying the ratio of first electrically conductive particles contained in a non conductive binder so that the resulting mixture has a granular and/or frangible crumb structure where some granules are connected to one another. The method may include the further step of milling the resulting mixture to break apart a frangible crumb structure into coated granules with a mill that is configured to break apart connected granules. Typically, the parts of the mill acting on the frangible club structure are spaced apart.

The method may include the further step of applying the mixture to a non-conductive substrate.

The method may comprising the further step of drying the mixture.

The proportion of magnetite to binder may be greater than or equal to 75% or 83% by weight. The resulting mixture may comprise a frangible crumb structure.

According to a third aspect of the invention there is provided a sensor comprising an electrical charge storage medium of the first aspect of the invention and spaced apart electrodes attached to the charge storage medium, and wherein the space defined by the space between the electrodes and the extent of the electrodes defines an active area.

Preferably, the spaced apart electrodes extend into the electrical charge storage medium by a distance.

The charge storage medium may be applied to a non-conductive substrate and wherein the spaced apart electrodes are attached to a top surface of the charge storage medium.

Preferably, the charge storage medium is applied to the non-conductive substrate in a thickness of between 50 and 250 micron.

Preferably, the charge storage medium is applied to the non-conductive substrate in a thickness of between 100 and 150 micron.

The sensor may further comprise a voltage source connected to the spaced apart electrodes.

The voltage may be applied for a specific time period or continuously in a pulsed rising or falling form and is either polarised or not polarised The voltage source may be configured to apply a voltage at a level that causes the electrical charge storage medium to lock into a state of conduction.

The sensor may be a volatile organic compound (VOC) sensor.

The non-conductive binder may be sensitive to a selected volatile organic compound or family of volatile organic compounds.

The electrical charge storage medium may be adapted to be sensitive to at least one of the volatile organic compounds including acetone.

The sensor may further comprise a measuring device attached to the electrodes and configured to measure a parameter indicative of resistance.

Preferably, the measuring device is an ohm meter or an ammeter.

The sensor may further comprise a resetting means configured to reset the conductive state of the electrical charge storage medium, the resetting means including a switch arranged to connect selectively the voltage source to the electrical charge storage medium.

Aspect ratio in relation to a particle is the ratio of the width of the particle to its height. A low aspect ratio means that the height to width ration is approaching 1:1.

Volatile organic compounds (VOCs) are organic chemicals that have a high vapour pressure at ordinary room temperature. Their high vapour pressure results from a low boiling point, which causes large numbers of molecules to evaporate or sublimate from the liquid or solid form of the compound and enter the surrounding air. VOCs are numerous and varied. They include both human-made and naturally occurring chemical compounds. For example, most scents or odors are of VOCs.

There are many reasons why it may be desirable to sense VOCs. Some are very harmful to humans, animal and plant health and are regulated by law. Others are known to be symptomatic of certain health conditions. For example, acetone on the breath can be associated with diabetes.

It would therefore be desirable to provide an improved sensor capable of sensing the presence of VOC's.

It would be desirable to provide an improved sensor capable of determining a concentration of VOC present in a sample.

It would be desirable to provide an improved sensor capable of sensing the presence of and/or the concentration of a specified VOC, for example acetone.

DESCRIPTION OF THE INVENTION

The Magnif range of magnetite produced by LKAB of Sweden has been found to be particularly useful in the invention as it has been found to have unusual electrical qualities with low electrical noise and stable, controllable charge and discharge parameters.

A super-sensor can be produced by mixing different sizes of magnetite particles with a water-based polyurethane binder in quantities which exceed the normal percolation loading for magnetite. LKAB Magnif ranges of magnetite bound with Witcobond 781 water based polyurethane have been used to produce thermo-setting ink versions of the invention. Other types of thermoset and thermoplastic polymer binders may be used in these composites to enhance their physical, chemical or electrical response to different types of analytes and forces.

Other types of conductive/semi-conductive particles and particle shapes including other sources of magnetite as well as different polymer binders can be used in this invention, alone or in combination, including with the LKAB magnetite materials, to produce different types of sensing capability, response, sensitivity and charge characteristics in the final composite. Mixing the components of the composite is done using a low shear paddle or folding regime until the mix just achieves homogeneity. Mixing is then complete and the polymer component can be cross-linked/set if required for immediate use or stored for later use.

Table 1 below illustrates the particle distributions for the different specifications of magnetite for three different grades of magnetite available from LKAB (Example 1 is LKAB Magnif 10, Example 2 is LKAB Magnif 25 and Example 3 is LKAB Magnif 50):

| Particle size distribution (cyclosizer method) | Example 1 Magnetite | Example 2 Magnetite | Example 3 Magnetite |
|---|---|---|---|
| d10 (micron) | 5 | 6 | 9 |
| d50 (micron) | 10 | 22 | 63 |
| d90 (micron) | 25 | 50 | 180 |
| particle characteristics | irregularly shaped, low aspect ration | | |

Chemical analysis of three grades of magnetite from the Magnif range produced by LKAB os Sweden are set out in Table 2. As can be seen, the material in all example is over 98% Fe3O4.

TABLE 2

Typical Values for LKAB Magnetite

| MAGNIF | 10 Example 1 | 25 Example 2 | 50 Example 3 | |
|---|---|---|---|---|
| Fe3O4 | 98.7 | 98.4 | 98.7 | % |
| MnO | 0.05 | 0.05 | 0.05 | % |
| CaO | 0.05 | 0.06 | 0.05 | % |
| MgO | 0.24 | 0.25 | 0.23 | % |
| Al2O3 | 0.22 | 0.22 | 0.2 | % |
| SiO2 | 0.16 | 0.27 | 0.11 | % |
| TiO2 | 0.35 | 0.33 | 0.25 | % |
| V2O5 | 0.26 | 0.27 | 0.24 | % |
| K2O | 0.004 | 0.003 | 0.004 | % |
| S | 32 | 32 | 32 | Ppm |
| Cl $_{water\ sol}$ | 10 | 10 | 10 | Ppm |
| Fe | 71.4 | 71.2 | 71.4 | % |
| Particle density | 5.2 | 5.2 | 5.2 | g/cm3 |
| Bulk density | around 2-3 g/cm3 | | | |

Charge is applied to the finished composite by applying a voltage through electrodes in contact with the composite. A DC voltage of as low as 30 volts has been found to impart a charge to the composite. A DC voltage of 50 volts may be used. A piezo spark generator has also been used to achieve a higher charged state and in all cases only low currents are required. The effect of applying charge is to change the quiescent, very low-conduction state of the composite, to become more conductive. This makes the composite more responsive to forces or the presence of analytes. Charge can be imparted in a fraction of a second using either a low or high voltage and can be topped up periodically to replace lost charge if continuous sensing is required. 'Look-through' sensing, similar to radar, is also possible with periodic charging.

These polymer compositions may be useful in the manufacture of sensors capable of sensing, VOCs, ionizing radiation, non-ionizing radiation, temperature, force, pressure, chemical species, and biological species. For example, a particular biological species may be known to release certain VOC(s). A chemical species when heated may release certain VOC(s). A polymer binder known to absorb the certain VOC(s) will react and increase the resistance of the charged composite. The polymer binder may expand and increase the resistance of the charged composite when contacted by certain VOC(s).

Figure 1A:
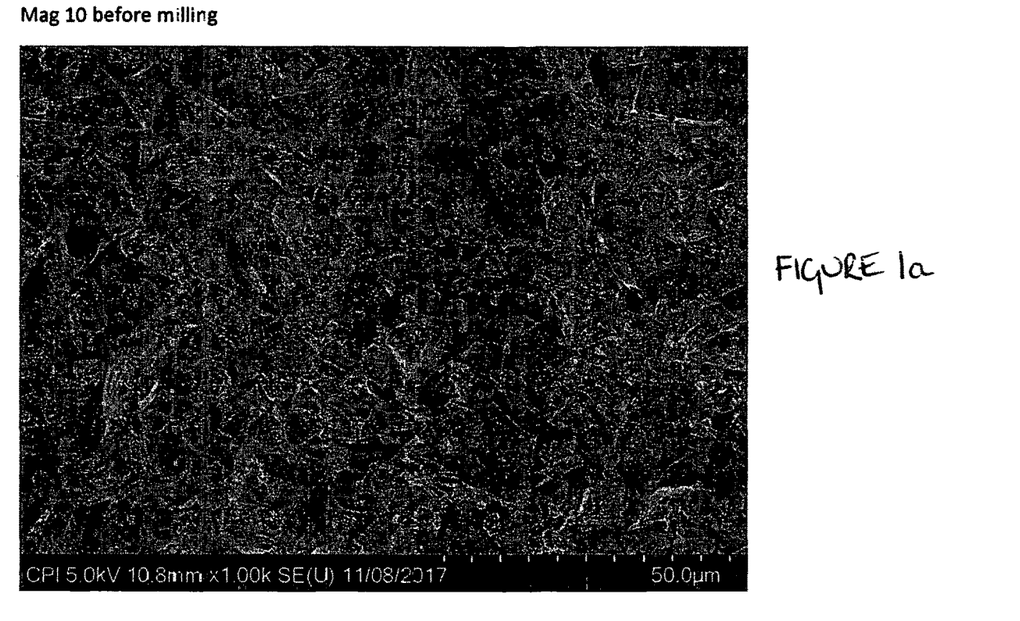
FIG. 1a is a micrograph of a distribution of particles of magnetite of Example 1.
Figure 1B:
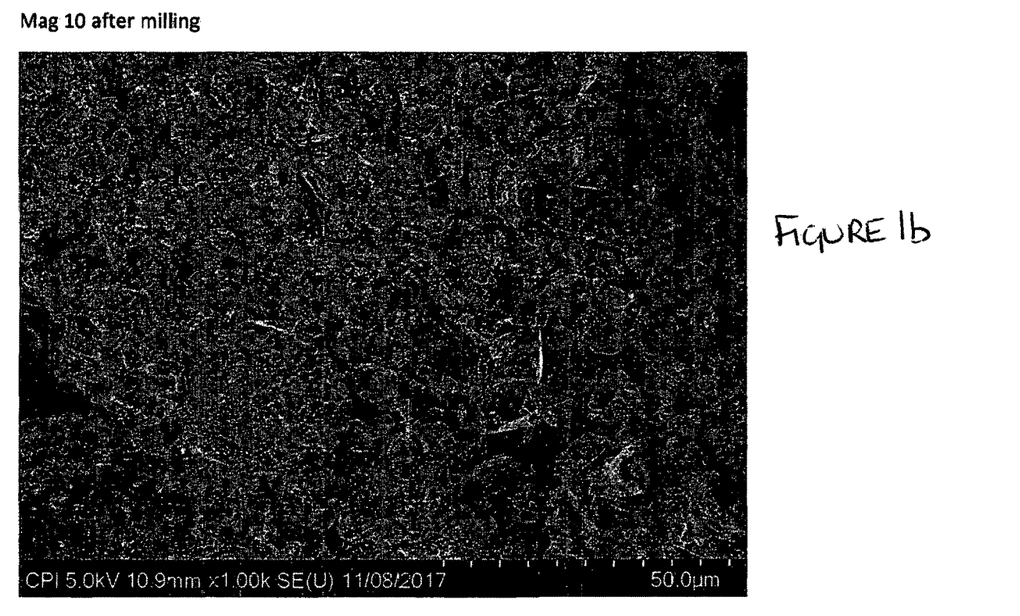
FIG. 1b is a micrograph of a distribution of particles of magnetite of Example 1 after a milling process.
Figure 2A:
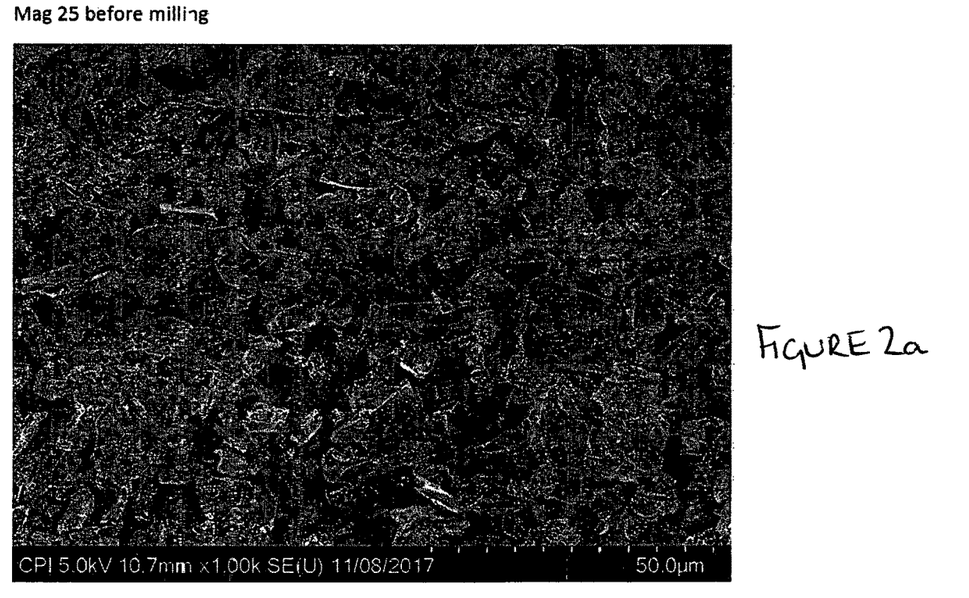
FIG. 2a is a micrograph of a distribution of particles of magnetite of Example 2.
Figure 2B:
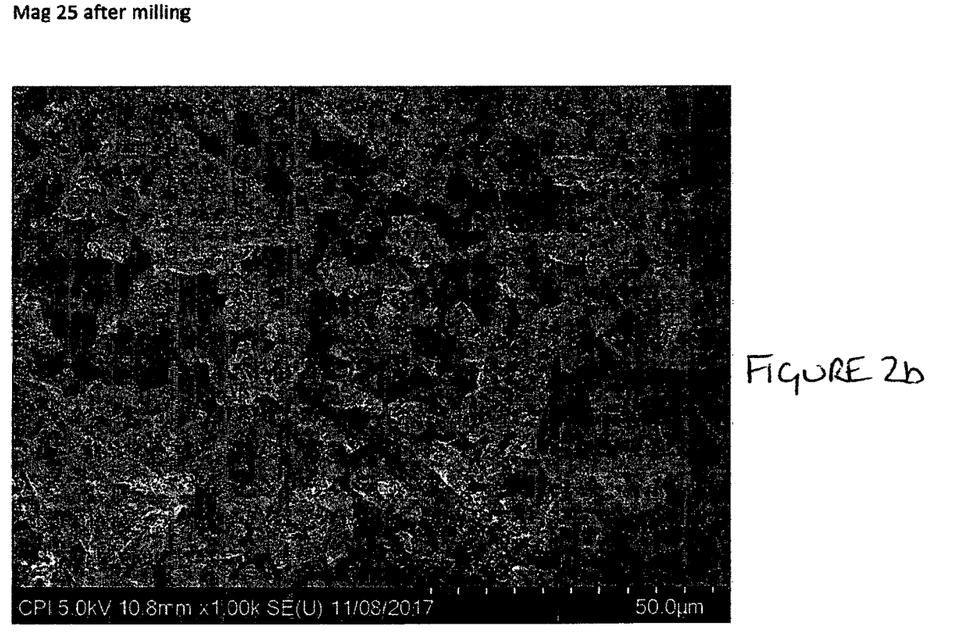
FIG. 2b is a micrograph of a distribution of particles of magnetite of Example 2 after a milling process.
Figure 3A:
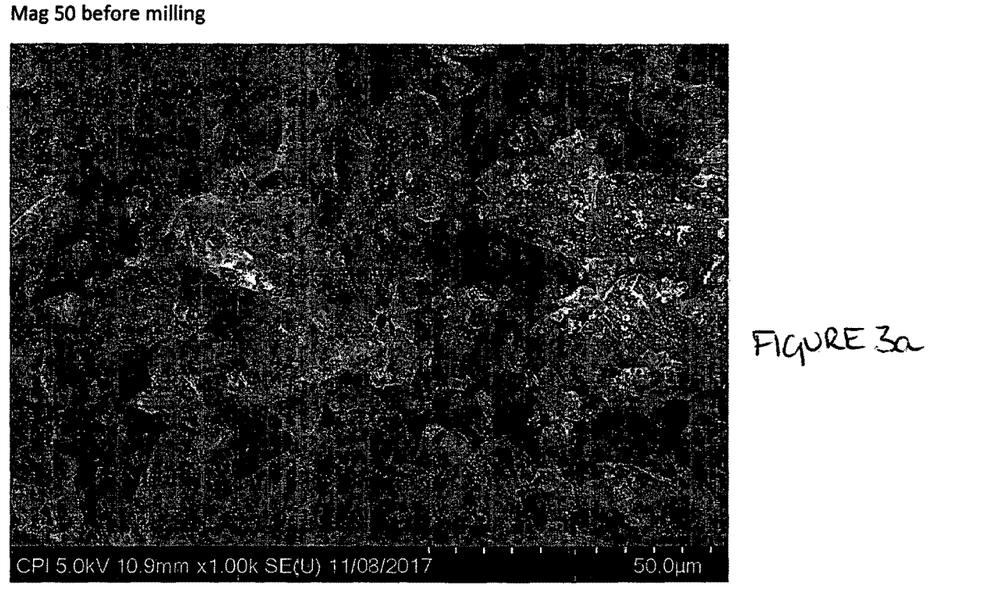
FIG. 3a is a micrograph of a distribution of particles of magnetite of Example 3.
Figure 3B:
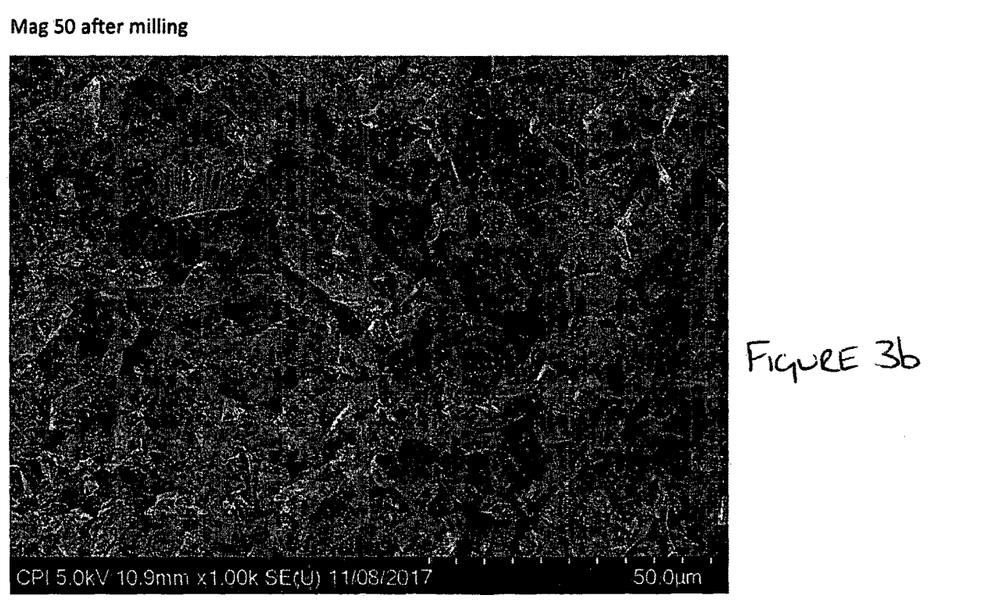
FIG. 3b is a micrograph of a distribution of particles of magnetite of Example 3 after a milling process.

All 3 products of the LKAB magnetite range can be used in the invention but I will describe the Magnif 50 as it gives the most sensitive performance of the range. If required, sensitivity can be reduced by the addition of synthetic magnetite to the Magnif magnetite. Synthetic magnetite is typically substantially spherical in shape. Sensitivity can be increased by the addition of dendritic silver powder. Other metals of different shapes may also be utilised to change sensitivity. Sensitivity may also be changed by further comminuting and/or classification of the base Magnif material to remove particles in identified size ranges. FIGS. 1b, 2b and 3b are micro-graphs illustrating particle shapes and sizes after milling of three different size grades of magnetite. The micro-graphs of FIGS. 1a, 2a and 3a show the corresponding grade of magnetite prior to size reduction through milling. In each case when the milled magnetite is mixed with a polymer the resulting composite is less sensitive than a composite made by mixing the magnetite that has not been milled with the polymer, that is sensitivity increases with increasing particle size. In this instance the term, "sensitivity" means that the magnitude of change in resistance resulting from an external input, such as the presence of a VOC, a bidder change in resistance meaning that the composite material is more sensitive.

To make a sensing composite LKAB magnetite Magnif 50 was functionalised by coating it with Witcobond 781 liquid polymer thinned down with 2 parts water to 1 part 781 polymer. This ratio can be changed and effects recovery, sensitivity and background noise levels in the finished composite. Dry Magnif 50 magnetite was added to the polymer/water solution in the ratio of 3 parts of magnetite to 1 part polymer/water solution by weight. The mix is stirred using low shear mixer until it just becomes homogenous as seen by a sheen on the surface of the mix. The mixing is complete at that point and the product can be used in the wet form as a coating or printing ink and then dried with the application of heat, blown air or microwaves as the 781 polymer is a thermoset. Other polymers can be used and polymers with specified absorption levels to specific VOC analytes can be chosen to provide VOC selectivity to the sensor. Where the polymer is a polyurethane for example the composite provides a large resistance change to acetone.

Where it is desired to create granules comprising single or agglomerated particles of magnetite the amount of polymer used is decreased when compared to the ratios described above, which will produce a solid material when cool and dry. The ratio of magnetite to polymer is increase to 6 parts of magnetite to 1 part of polymer water solution by weight made as described above using the same type of magnetite and polymer, that is 1 part to polymer to 2 parts water. By reducing the amount of polymer the resulting mixture is very dry and may be described as a frangible crumb. Where adjacent granules are connected together they can be broken apart by passing the mixture through a mill that is arranged to break apart joined granules rather than reduce the size of individual granules. For example, a mill comprising rollers that are arrange with a small space therebetween could be used. It may be of advantage to use rollers having a relatively soft surface, such as rubber, rather than steel or other rollers. Nevertheless, the method of producing a granular form of the composite material of the invention is not limited to any particular type of mill.

Figure 4A:
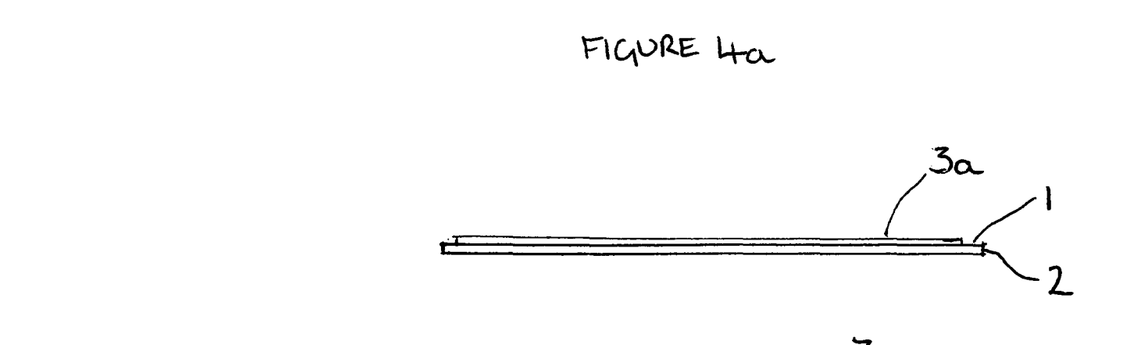
FIG. 4a is a side view of a sensor according to an aspect of the invention.
Figure 4B:
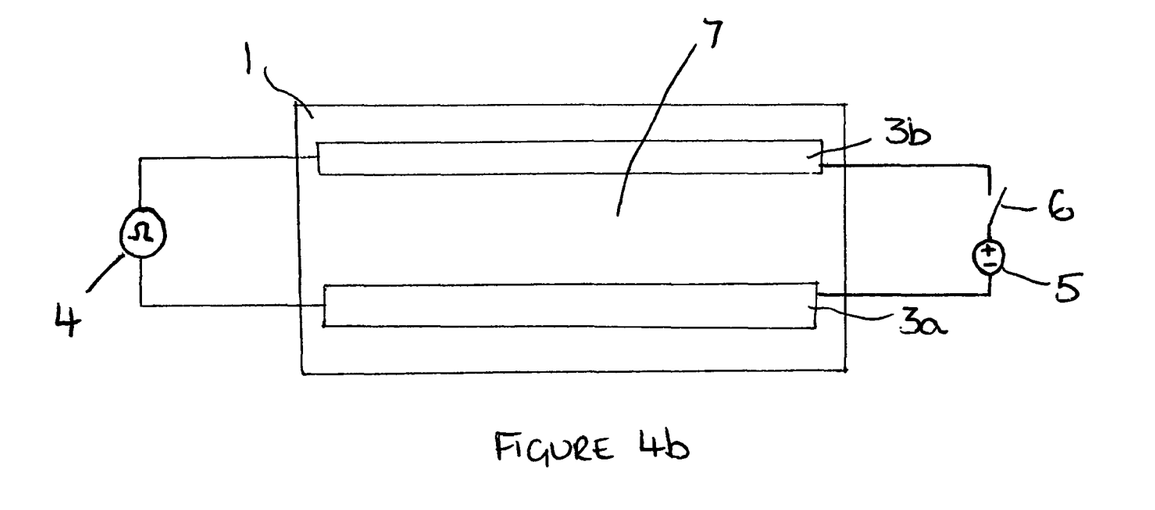
FIG. 4b is a plan view of the sensor illustrated in FIG. 4b.

A sensor is illustrated in FIGS. 4a and 4b. The illustrated sensor comprises a layer 1 of composite ink comprising the charge storage medium of the invention applied to the surface of a non-conductive layer of material 2. The non-conductive material may be plastic, film, paper, card, textile or foam for example. Where the non-conductive material has a three dimensional structure, such as a textile or foam, the composite ink may be applied the structure thereof.

In its simplest form a sensor will comprise a 100 to 150 micron coating of the ink on a non-conductive surface.

Where the material has a three dimensional structure, such as a textile or foam, the composite ink may be applied the structure thereof.

Two conductive electrodes 3a, 3b are attached to the top surface of the dried ink with a conductive adhesive. These electrodes are arranged to have a gap between them which forms the area 7 sensitive to the analyte VOC. The width of the gap can be from 100 micron to a few mm and its dimensions form the active area of the sensor. The length of the gap in the electrodes can be from 100 microns to many centimetres depending on the area requiring exposure to the analyte.

Figure 5:
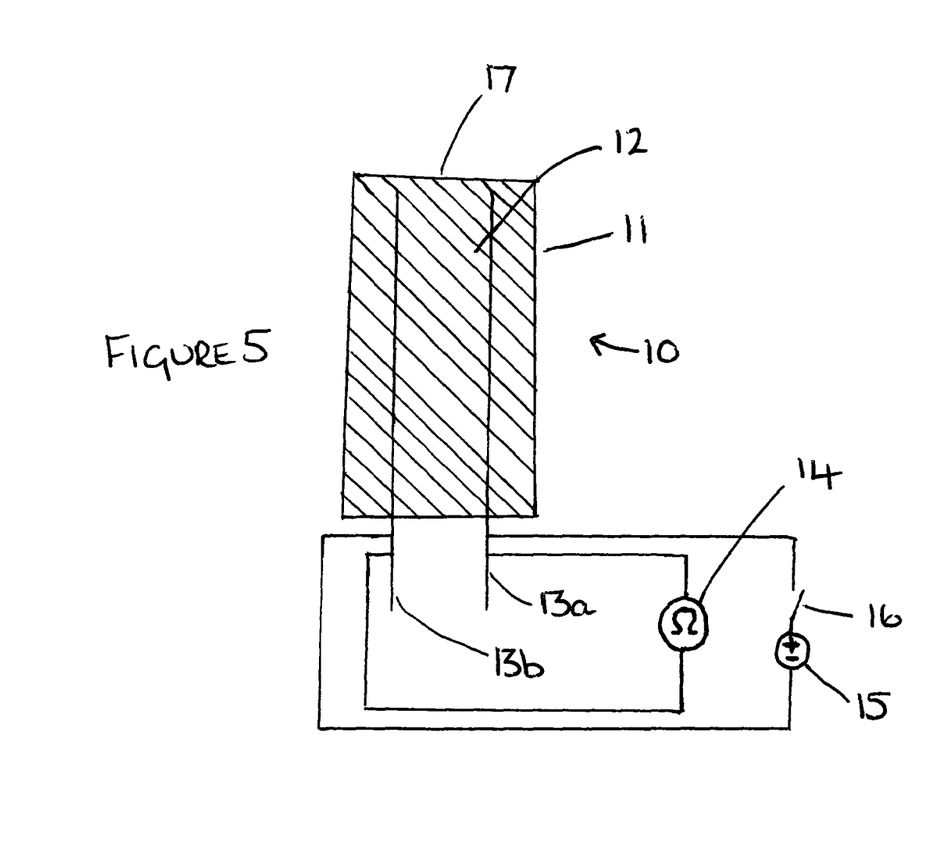
FIG. 5 is a schematic representation of a sensor according to another embodiment of the invention.

FIG. 5 illustrates an alternative embodiment of a sensor. The sensor 10 of FIG. 5 comprises a non-conductive container 11 filled with a composite material of electrical charge storage medium 12 indicated by the cross-hatched lines. Electrodes 13a, 13b extend through a bottom wall of the container 11 into the charge storage medium. An area 17 sensitive to analyte is formed at an open end of the container. The charge storage medium may be in a number of forms. For example, the charge storage medium may be formed by pouring electrical charge storage medium into the container whilst medium is in a pourable state. The medium may be heated to reduce its viscosity to facilitate such pouring. The medium, once poured into the container 11 then sets over a period of time. Alternatively, the medium may be provided by filing the container with a matrix of granules, the granules being formed by coating individual particles and/or agglomerations of particles of magnetite with the selected polymer binder. In another alternative the medium may be carried on a foam carrier which is shaped and dimensioned to fit the container 11.

In the embodiments of FIGS. 4a, 4b and 5 the electrodes 3a, 13a, 3b, 13b are connected to an ohm meter 6, 16 for detecting a change resistance of the medium 1, 12 and a voltage source 5, 15. A switch 6, 16 is provided for connecting the voltage source 5, 15 to the electrodes 3a, 13a, 3b, 13b selectively. The voltage source is used to apply a charge to the medium causing a change its resistance.

The sensing composite, that is the electrical charge storage medium of the invention, has a quiescent resistance state of more than $10^9$ Ohms but surprisingly it has been found that the resistance can be reduced by the application of a voltage. This effect is immediately apparent on application of the voltage.

The voltage can be applied in a constant, pulsed, rising or falling form and does not need to be polarised. A low voltage produces a smaller effect which although transient, is related to the voltage level. A higher voltage produces a larger effect, that is the resistance of the material is reduced more. At a certain voltage level, this transient behaviour disappears and the composite stays in a locked holding state of conduction. It is this locked state that provides the composite with the best start condition for detecting the presence of a VOC. The VOC interacts with the polymer of the composite unlocking the holding state. It is believed that the VOC causes the polymer to swell initially unlocking the holding state. Once unlocked, the initial low resistance of the composite in the holding state increases towards the quiescent high resistance state whilst the sensor is exposed to an analyte. The response is surprisingly rapid and can cover more than 4 orders of resistance change in under 1 second. Also surprisingly, if the analyte is removed, the resistance change will stop within a second and return to a level very close to the charged start state within a few seconds. Alternatively, the composite can also be returned to its charged state instantly by applying a further charge. Whichever way the sensor achieves the charged state, it is immediately ready to detect an analyte.

Test:

For the test, acetone vapour was blown from a rubber bulb onto the sensor from a distance of 5 cm for 1 second.

The charge used for the Magnif 50 sensor detailed above was produced by applying a DC voltage pulse of $1K_V$ limited to 1 mA for 100 mS to the sensor which initially showed a resistance above measurable limits of $10^9$ Ohms This resulted in an immediate locked state resistance in the sensor composite of 100 KOhms.

The first exposure to Acetone produced an increase in resistance to more than $10^9$ Ohms in less than 1 second. After removal of the vapour the sensor self-recovered to 550 KOhms in 10 seconds.

A second test (as paral) was conducted immediately after the above-mentioned 10 second interval and the sensor showed an increase in resistance to more than $10^9$ Ohms in less than 1 second and self-recovered to 1.5 MOhms in 10 seconds.

A third test produced a similar response but the return was to 2.7 MOhms

A fourth test produced a similar response but the return was to 2.0 MOhms

A fifth test produced a similar response but the return was to 2.4 MOhms.

A test was then conducted on the same sensor by applying a $1K_V$ charge to reset the sensor after each acetone activation. This test was conducted 5 times and the sensor went into an immediate locked state of 100 KOhms on each occasion after a sensing activation. The interval between activations was 30 seconds and on each occasion the resistance to the exposure was above $10^9$ Ohms.

The invention claimed is:

1. An electrical charge storage medium comprising:
   a quantity of first electrically conductive particles;
   a non conductive binder, wherein the quantity of first electrically conductive particles are contained in and dispersed through the non conductive binder;
   wherein the first electrically conductive particles are magnetite particles, and wherein the quantity of magnetite particles includes a distribution of particle sizes between sub-micron and tens of microns, and wherein the magnetite particles have a plurality of planar faces, adjacent planar faces connected at a vertex, the particles each having a plurality of vertices, wherein at least some of the magnetite particles are irregular in shape;
   wherein the irregularly shaped magnetite particles are different in shape from other magnetite particles within said quantity of magnetite particles; and
   wherein the non-conductive binder forms a layer around each magnetite particle of the quantity thereof such that said magnetite particles are separated from one another by said non-conductive binder in which the said magnetite particles are contained and dispersed.

2. An electrical charge storage medium according to claim 1, wherein the shape of some of the first electrically conductive particles in the distribution fall under at least "oblate", that is tabular, and others of the first electrically conductive particles in the distribution fall under at least "bladed", that is a flat or elongated shape form.

3. An electrical charge storage medium composition according to claim 1, wherein in the distribution of particles the particle size of the first electrically conductive particles at $d_{50}$ is one of:
   between 50 and 75 micron;

between 60 and 65 micron;
between 20 and 25 micron;
between 5 and 15 micron; and
10 micron.

4. An electrical charge storage medium according to claim 1, wherein the distribution of particle sizes between sub-micron and tens of microns in the quantity of magnetite particles includes sub-micron sized particles and particles that are tens of microns in size.

5. An electrical charge storage medium according to claim 1, further comprising a second type of electrically conductive particle of a different shape to the first electrically conductive particle.

6. An electrical charge storage medium according to claim 5, wherein the second type of electrically conductive particle is characterised by at least one of:
    having one of the following shapes: void bearing, plate like, needle like and spherical;
    being selected from the group comprising: silver, nickel, copper, iron, oxides of silver, nickel copper and iron including but not limited to magnetite and synthetic magnetite; and
    having a particle size between 10 and 15 micron.

7. An electrical charge storage medium according to claim 1, wherein the binder is a polymer binder.

8. An electrical charge storage medium according to claim 7, wherein the polymer is one of: a silicone polymer, a polyurethane polymer; polyethylene and an acrylic polymer.

9. An electrical charge storage medium according to claim 1, wherein the thickness of the layer is in the order of 10 nano-metres.

10. An electrical charge storage medium according to claim 1, wherein the particles are coated with the thin layer of binder and wherein adjacent separate coated particles are in contact with each other and wherein the charge storage medium is formed by a matrix of so coated particles.

11. An electrical charge storage medium according to claim 1, wherein the proportion of magnetite particles to binder is one of:
    greater than or equal to 33% by weight;
    greater than or equal to 75% by weight;
    greater than or equal to 90% by weight.

12. An electrical charge storage medium according to claim 1, wherein the ratio of first electrically conductive particles contained in the non conductive binder is configured such that the resulting mixture has a granular form.

13. An electrical charge storage medium according to claim 12, wherein the proportion of magnetite to non conductive binder is greater than or equal to 75% by weight.

* * * * *